United States Patent
Kivi et al.

(10) Patent No.: US 10,995,134 B2
(45) Date of Patent: May 4, 2021

(54) METHOD FOR DEVELOPMENT OF MONOCLONAL ANTIBODIES

(71) Applicant: Icosagen Cell Factory OÜ, Tartumaa (EE)

(72) Inventors: Gaily Kivi, Ülenurme (EE); Kaupo Teesalu, Ülenurme (EE); Jüri Parik, Ülenurme (EE); Mart Ustav, Ülenurme (EE); Andres Männik, Ülenurme (EE)

(73) Assignee: Icosagen Cell Factoey Oil, Ülenurme (EE)

( * ) Notice: Subject to any disclaimer, the term of this patent is extended or adjusted under 35 U.S.C. 154(b) by 508 days.

(21) Appl. No.: 15/764,990

(22) PCT Filed: Sep. 30, 2016

(86) PCT No.: PCT/EP2016/073524
§ 371 (c)(1),
(2) Date: Mar. 30, 2018

(87) PCT Pub. No.: WO2017/055617
PCT Pub. Date: Apr. 6, 2017

(65) Prior Publication Data
US 2018/0273611 A1    Sep. 27, 2018

Related U.S. Application Data

(60) Provisional application No. 62/234,927, filed on Sep. 30, 2015.

(51) Int. Cl.
C07K 16/08     (2006.01)
C07K 16/00     (2006.01)
C07K 16/10     (2006.01)
C07K 16/40     (2006.01)
C07K 16/22     (2006.01)

(52) U.S. Cl.
CPC ............. *C07K 16/10* (2013.01); *C07K 16/00* (2013.01); *C07K 16/084* (2013.01); *C07K 16/22* (2013.01); *C07K 16/40* (2013.01); *C07K 2317/14* (2013.01); *C07K 2317/33* (2013.01); *C07K 2317/56* (2013.01); *C07K 2317/622* (2013.01)

(58) Field of Classification Search
CPC ............ C07K 2317/33; C07K 2317/14; C07K 2317/56; C07K 2317/622
See application file for complete search history.

(56) References Cited

FOREIGN PATENT DOCUMENTS

WO    2004/106377 A1    12/2004

OTHER PUBLICATIONS

Andris-Widhopf, J. et al. "Methods for the generation of chicken monoclonal antibody fragments by phage dispaly", J. Immunol Methods 2000, vol. 242, No. 1-2, pp. 159-181.
Schaefer, J. V. et al "Construction of scFv fragments from hybridoma or spleen cells by PCR assembly". In: Antibody Engineering. Edited by Kontermann R., Dübel S., vol. 1, 2nd edn. Heidelberg: Springer; 2010: 21-44.

(Continued)

*Primary Examiner* — Jeremy C Flinders
(74) *Attorney, Agent, or Firm* — Berggren LLP

(57) ABSTRACT

This invention provides a method and a kit for rapid and robust development monoclonal antibodies. The method does not require hybrid technologies nor does it require single cell manipulations. The method allows elimination of cross-target antibodies.

11 Claims, 6 Drawing Sheets

Specification includes a Sequence Listing.

(56) References Cited

OTHER PUBLICATIONS

Rader, C. et al "The rabbit antibody repertoire as a novel source for the generation of therapeutic human antibodies", J Biol Chem 2000, vol. 275, No. 18, pp. 13668-13676.
Quan, J. et al. "Circular polymerase extension cloning for high-throughput cloning of complex and combinatorial DNA libraries", Nat Protoc 2011, vol. 6, No. 2, pp. 242-251.
Karro, K. et al. "DNA transfer into animal cells using stearylated CPP based transfection reagent", Methods Mol Biol 2015, vol. 1324, pp. 435-445.
Hall, T. A.: "Bio Edit: a user-friendly biological sequence alignment editor and analysis program for Windows 95/98/ NT", Nucl Acids Sym Ser 1999, vol. 41, pp. 95-98.
Ligthwood, D. J. et al. "Antibody generation through B cell panning on antigen followed by in situ culture and direct RT-PCR on cells harvested en masse from antigen-positive wells", Journal of Immunological Methods, Elsevier Science Publishers B.V., Amsterdam, NL, vol. 316, No. 1-2, Oct. 30, 2006, pp. 133-143, XP028017643, ISSN: 0022-1759, DOI: 10.1016/J.JIM.2006.08.010 [retrieved on Oct. 30, 2006].
Seeber, S. et al. "A robust high throughput platform to generate functional recombinant monoclonal antibodies using rabbit B cells from peripheral blood", PLOS ONE, vol. 9, No. 2, Feb. 4, 2014, pp. e86184/-14, XP055128871, US, ISSN: 1932-6203, DOI: 10.1371/journal.pone.0086184.
Tiller, T.: "Single B cell antibody technologies", New Biotechnology, vol. 28, No. 5, 2011, pp. 453-457, XP028290739, ISSN: 1871-6784, DOI: 10.1016/J.NBT.2011.03.014 [retrieved on Apr. 5, 2011].
Kivi, G. et al. "HybriFree: a robust and rapid method for the development of monoclonal antibodies from different host species", BMC Biotechnology, vol. 31, No. 1, Dec. 1, 2016, p. 58, XP055332655, DOI: 10.1186/ s12896-016-0232-6.

METHOD FOR DEVELOPMENT OF MONOCLONAL ANTIBODIES

PRIORITY

This application is a U.S. national application of the international application number PCT/EP2016/073524 filed on Sep. 30, 2016 and claiming priority of U.S. provisional application No. 62/234,927 filed on Sep. 30, 2015, the contents of both of which are incorporated herein by reference.

SEQUENCE LISTING

This application includes a sequence listing provided in a computer readable format.

FIELD OF THE INVENTION

This invention relates to methods and kits to develop monoclonal antibodies specifically suitable for recombinant production in mammalian cell systems.

BACKGROUND

Development of monoclonal antibodies that can be recombinantly produced in mammalian cell cultures has high priority goal in research and medical areas. The crucial step in this process is determination the sequences of antigen binding domains of antibodies with desired properties. Many different techniques are described for this but these techniques also have shortcomings related to time-consumption, cost or efficiency of sequence production. For these reason there is a need for a robust, rapid, inexpensive and flexible method for development of monoclonal antibodies suitable for production in mammalian cell factories.

Generally, monoclonal antibodies (MAbs) are made by identical immune cells and they have monovalent or monospecific affinity: they bind to the same epitope. However, there are antibodies, which are produced by completely different, non-identical immune cells, which bind to the same epitope. The high affinity and selective binding of MAbs to their antigens make them highly potent for use in biochemistry, molecular biology and medicine.

Historically, the first method for isolation of monoclonal antibodies was hybridoma technology. This technology is based on forming hybrid cell lines (hybridomas) by fusion of antibody-producing B cell with a myeloma cell. The antibodies produced by the particular hybridoma clone are all of a single specificity. Thus, single clones are screened for identification of antibody with desired properties. However, the production of the MAbs by hybridoma technology has also some shortcomings: the process needs relatively long time (up to several months) and has complications if applied to organisms other than murine species. Moreover, no antibody sequence information becomes directly available by the method. Thus, when the hybridoma screened antibody is selected for further development (e.g. for developing therapeutic products), the variable domains of heavy (VH) and light chain (VL) that together determine antibody's antigen binding properties must be isolated from the hybridoma cells and sequenced. Sequence data is ultimately needed for recombinant production of the final MAb product as well as for improvements, such as humanization, isotype conversion, affinity maturation etc.

In contrast, recombinant antibody isolation technologies usually do not include hybrid cell line step but involve obtaining of VH and VL domain sequences from antibody expressing source cells (e.g. B-cells from spleen, bone marrow or blood). Commonly, VH and VL cDNAs are amplified by RT-PCR using mRNA isolated from the cells. By combinatory library based strategies large repertoire of different VH and VL sequences are amplified from population of cells (e.g. millions of B-cells isolated from immunized animal). Thereafter, the amplified products are used for construction of combinatory libraries by random pairing of VH and VL domains. Thus, combinatory strategies necessarily involve the screening step for identification of the antibodies (VH and VL combinations) with desired properties from large libraries. These screening methods involve in vitro antibody display techniques, such as phage display and ribosome display, as well as in vivo display platforms, such as bacterial, yeast, and recently also mammalian cell-surface displays. Mammalian cell display has a number of features which are advantageous for selecting antibodies for recombinant production. For example, using mammalian cells for screening ensures that later there will be no loss of activity of MAb when the antibody is produced as natural post-translationally modified IgG molecule in mammalian cells. Loss of activity is a complication sometimes associated with MAbs screened in phage, bacterial and even yeast display systems. Instead, performing the screening in mammalian cells ensures that recovered active antibody is synthesized, modified, assembled and secreted through the authentic mammalian cellular pathways.

The recombinant methods also include non-combinatorial strategies that are based on retrieving of antibody sequences from single B-cell or clonally expanded progeny of the single cell. By this way the original heavy and light chain pairs are kept together during the development process. This can be achieved by amplification of re-arranged VH and VL region cDNAs from one particular B-cell by a technically challenging single-cell RT-PCR based methods. Also the isolated single B-cells can be amplified in cell culture. The methods include immortalization of the differentiated B-cells, e.g. using Epstein-Barr virus (EBV), retroviral oncogenes, TLR ligands, or cultivation in specific conditions with irradiated thymoma cells or using IL4 treatment and CD40 triggering. In addition, techniques are developed for facilitating or increasing the efficiency of the non-combinatorial strategies, e.g. by enrichment of source B-cells that express the antibodies with desired affinity. For example lymphocyte capturing (panning) has been used on the antigen coated surface for establishment of retained B-cell cultures that were used as source of VH and VL sequences. Microwell array chip assay or fluorescence based sorting methods have been used for identification and isolation of cells secreting antibodies with desired properties. However, all of the non-combinatory methods involve either complicated single-cell manipulations and/or establishment of sterile primary cell cultures from biological materials, specialized equipment and expensive supplements.

The methods, and the kit described here below provide solutions to the shortcomings of the currently existing technologies.

SUMMARY OF THE INVENTION

A novel technology is described here for development of monoclonal antibodies. The method combines elements from combinatorial and non-combinatorial strategies and the screening is done using mammalian cells. The method has unique features that allow high recovery rate of developed antibodies. The method is universal and applicable to any species for which the antibody sequence information is available for designing the primers for VH and VL cDNA amplification. The key property of the technology is rapid and robust workflow: it takes about 10 days from source material collection to sequence information, and it does not need establishment of sterile B-cell cultures, single cell manipulations or specialized materials. Additionally, the method can optionally include negative selection step to eliminate the isolation of antibodies directed to undesired off-targets.

The technology is illustrated here by detailed examples of recovering mouse, rabbit and chicken monoclonal antibody sequences from immunized animals. The antibodies are shown to be functional in different immunoassays, like ELISA, immunofluorescence and Western blot. In addition, specific example illustrates optional modification of the method by negative selection step used for avoiding the recovery of antibodies directed to undesired off-targets.

It is an object of this invention to provide a rapid and robust method to develop monoclonal antibodies.

It is an object of this invention to provide a method to develop monoclonal antibodies, said method comprising the steps of:
 a) Capturing source cells expressing antigen specific antibodies on a solid matrix covered with the antigen;
 b) Amplifying variable heavy chain (VH) and variable light chain (VL) cDNA from the captured cells;
 c) Constructing a VH-VL combinatory library in a mammalian expression vector; and
 d) Identifying proper VH-VL combinations using mammalian screen.
 e) Construction of authentic monoclonal antibody from the VH and VL amplified sequences
 f) Identifying proper target-specific antibody expressed from the mammalian cells using the mammalian screen It is another object of this invention to provide a method to develop monoclonal antibodies wherein the source cells are spleen cells from crude homogenate of spleen from an immunized animal. The source cells may also be bone marrow or peripheral blood cells.

It is another object of this invention to provide a method to develop monoclonal virus neutralizing antibodies. The antibodies may be against HPV, Ebola, Chikungunya or HIV.

It is yet another object of this invention to provide a method to produce monoclonal antibodies, wherein after identifying a target specific antibody expressed from a mammalian cell the mammalian cells are cultured in large scale of antibody production.

It is a further object of this invention to provide a method to produce monoclonal antibodies where the antibodies are free from off target affinity.

Still another object of this invention is to provide a method to produce monoclonal antibodies for therapeutic use, vaccine production, especially for vaccines against viral infections.

It is yet another object of this invention to provide monoclonal antibodies produced by the method disclosed herein.

It is a further aspect of this invention to provide a kit for developing antibodies according to this disclosure.

DETAILED DESCRIPTION OF THE INVENTION

Definitions

By cross-reactive antibody it is meant an antibody that can bind to immunogen but it also has significant binding (reactivity) to an antigen that differs from the immunogen. By virus like particle (VLP) it is meant particles assembled in cells and bud from the cells due to expression of viral structural and/or envelope proteins.

By CHOEBNALT85 cell line it is meant a derivation of Chinese Hamster Ovary cell line expressing Epstein-Barr virus protein named EBNA1 and mouse polyoma virus protein named large T. The cell line is available from Icosagen Cell Factory, Estonia.

By QMCF vector it is meant plasmids carrying hybrid replicons comprised of mouse polyomavirus enhancerless core replication origin in combination with Epstein-Barr virus EBNA-1 protein binding sites (FR—Family of Repeats) as nuclear retention element. These proteins ensure stable replication and maintenance of QMCF expression vectors in QMCF cells, both obtainable from Icosagen Cell Factory, Estonia.

The method according to this disclosure can be used for rapid and reliable development of monoclonal antibodies that are subsequently produced in mammalian cells. The process is simple and does not need culturing of B-cells or single-cell manipulations. Moreover, the method does not require but customary molecular biology laboratory equipment. The method is applicable with any species for which an antibody cDNA sequence information is available.

Figure 1:
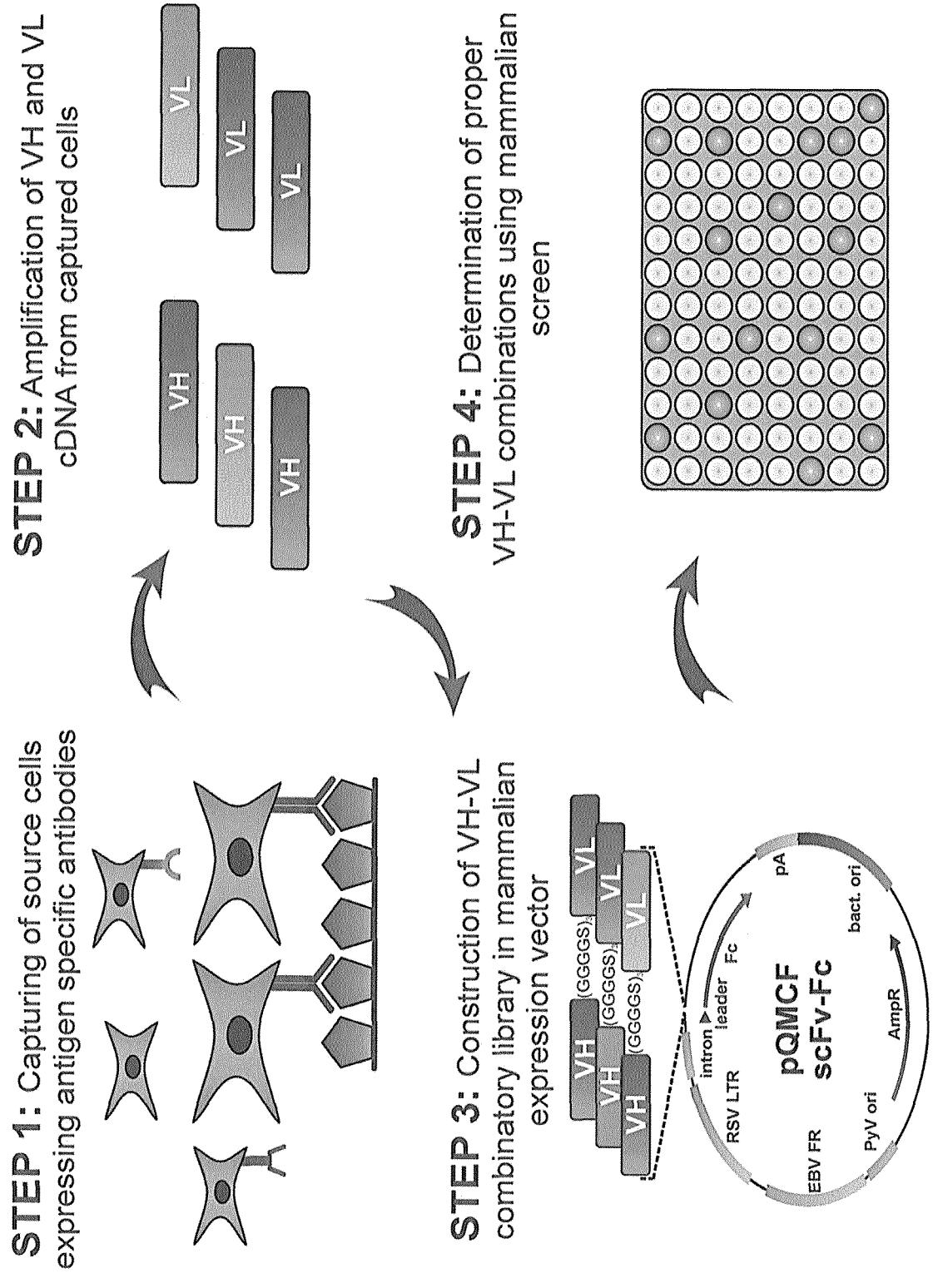
FIG. 1. General workflow of the HybriFree method. The key steps includes: (STEP 1) the enrichment of source material by capturing of specific antibody producers; (STEP 2) amplification of VH and VL cDNAs, (STEP 3) construction of combinatory VH-VL library in scFv-Fc (or IgG) expression plasmid DNA format, and (STEP 4) screening proper VH-VL combinations after expression of MAbs in mammalian cells.

The method is schematically shown in FIG. 1 and the key steps include: (i) enrichment of source material by capturing of specific cells on which surface the antibodies are exposed on the antigen loaded plastic surfaces; (ii) amplification of VH and VL coding cDNAs; (iii) construction of combinatorial VH-VL library mammalian expression plasmid DNA format; and (iv) identification of the proper specific antigen binding VH-VL combinations after antibody expression in mammalian cells. The screening is performed by transfection of individual DNAs into mammalian cells in multiwell (e.g. 96-well) format allowing screening of limited number of clones in a single round. To ensure that proper VH-VL combinations are discovered from limited number of clones, it is crucial to keep the diversity of library in narrow range by implying stringent conditions for the paratope-epitope interaction.

Preferably the library includes only those VH and VL regions that are found in the antibodies recognizing the antigen of interest. Here, the diversity limitation is achieved by functional selection of source cells before the VH and VL regions are isolated. This is ensured by capturing the source cells on the solid surface of ELISA plate well coated with the antigen of interest (step 1 in FIG. 1). The capture is performed via interactions between surface immunoglobulin (sIg) molecules on the source cell and the immobilized antigen. Crude homogenate of spleen containing the intact cells serves well as the source material in the method of this disclosure.

In order to ensure efficient and low-background capturing step the conditions of the capturing step were carefully adjusted and the adjustments were correlated with surprising improvements. The adjustments include capture medium containing 0.5% BSA and 0.1% (both w/v) $NaN_3$. Importantly, a significant improvement both in efficiency was obtained when $NaN_3$ was added into the capture medium. This is suggested to be related to blocking antibody internalization by the cells and/or RNA degradation under conditions of inhibited cellular metabolic activity by $NaN_3$. Other conditions adjusted are number of source cells taken per sample, capturing time which is sufficient for binding but not long enough for causing major degradation of RNA without de novo synthesis, and washing protocol for removal just loosely attached cells. These modifications are described in detail in examples below.

In the second step of the method, the captured source cells are directly subjected to RNA isolation and cDNA preparation (step 2 in FIG. 1) followed by construction of combinatory antibody library in mammalian expression vector (step 3 in FIG. 1).

The quality of the library can be evaluated by transfection of library pool DNA (mixture of all library members) DNA and analysing the secretion of antigen specific binders into culture medium. Single DNA clones prepared from bacterial colonies are transfected and antigen specific antibody production is evaluated for each clone for isolation of individual MAbs (step 4 in FIG. 1). Finally, VH and VL sequence information is identified for selected positive clones. In the examples provided below we have used modified CHO-S cell line CHOEBNALT85 for screening of the pool or individual clones of the antibodies. These cells grow in serum-free chemically defined medium and ensure high transfection efficiencies in variety of scales, including 96-well based high-throughput assay. In association with pQMCF vector the CHOEBNALT85 cells ensures relatively high transient production levels of IgG-like molecules (typically tens of micrograms per millilitre at 72 h time-point using 2 ml culture scale). Moreover, the same cells we routinely use for recombinant antibody production in larger scale. Using the same cells for screening and production gives good chances that there are no subsequent problems with productivity. However, a skilled artisan understands that any suitable expression vector or mammalian cell line that can be efficiently transfected with plasmid DNA can be used for the screening step of this method.

Isolation of antigen-specific VH and VL pairs in scFv-Fc screening certainly provides enough information for construction of expression vectors for recombinant production of natural IgG antibodies assembled by two heavy and two light chains that are expressed in the cells as separate polypeptides. However, cDNA re-synthesis (by PCR or gene synthesis), change of the expression vector and additional cloning steps are necessary. This makes the whole process cumbersome and time-consuming. Thus, we modified our method for screening the VH and VL combinations so that intact natural IgG molecules are formed instead of scFv-Fc antibodies.

Thus, there is need for MAbs recognizing specific target proteins or even protein isoforms but not off-target antigens sharing some homologous or even identical epitopes. We have met the problems that MAbs retrieved from immunizations with full-length proteins have unacceptable levels of cross-reactivity and it is cumbersome to sort out the small number of "right" MAbs from the population of recovered antibodies. Therefore we have introduced optional step to the method when the source cells are shortly pre-adsorbed with excessive amount of off-target antigen(s) prior capturing with desired target. By this way, all binding sites on the cells which are cross-reactive with non-desired targets can be saturated before and cannot bind to target antigen anymore.

The methods used in developing the invention is described below after which the method and kit of this invention is described by means of non limiting examples.

Methods

Immunization of Animals

Chicken: Six to 8 months old Hy-Line chickens were immunized by four (weeks 0, 2, 4 and 18) intramuscular (im) injections of 0.5 mg protein antigen in complete (initial immunization) or incomplete Freund adjuvant (subsequent immunizations). Antigen boost was given 2 weeks after final injection as 0.1 mg protein in PBS intravenously (iv).

Mice: Four to 6 weeks old female BalbC mice were initially immunized intraperitoneally (ip) with ~50 µg of protein antigen in complete Freund adjuvant (week 0) followed with 4 ip administrations (weeks 3, 7, 16, and 2 times in week 17) with same amount antigen in PBS. Rabbits: Approximately 5 month old New Zealand rabbits were initially immunized by 2 subscapular injections (into both side of body). The protein antigen or VLPs was administered 4-5 times in amount of 0.1-0.4 mg in complete Freund (first immunization only) adjuvant or in incomplete Freund adjuvant. Finally the response was boosted by intravenous injection of 0.1 mg protein antigen.

Collection, Storage and Preparation of Source Cells

After confirmation of antigen-specific antibody response in egg yolk preparations of chickens (IgY) or in blood serum of mice and rabbits (IgG), the spleens were collected 2-4 days after final immunization (boost). The animals were anesthetized and cardiac puncture was used to collect blood. The spleen was removed and stored in ice until preparation (within one hour). For preparation of cell homogenate, the spleen was homogenized in ice-cold PBS using 40 µm cell dissociation sieve. The material was collected into 50 ml cell culture tube, precipitated by centrifugation (300×g, 5 min, 4° C.). The cells were re-suspended in 50 ml of ice-cold PBS and centrifuged again. Finally the precipitated cells were suspended in 5 ml ice-cold freezing medium (heat inactivated foetal bovine serum+10% DMSO), distributed into cryovials (1 ml per tube) and frozen slowly to −80° C. For longer storage the tubes were transferred into liquid nitrogen after 4-5 days.

RNA Isolation and cDNA First-Strand Synthesis

For total RNA isolation, 200 µl TriReagent® (Molecular Research Center, US) and 1-2 µg of yeast tRNA (Life Technologies, US) were added per single well of the 96-well plate used for cell capturing. The RNA isolation was performed as provided by TriReagent® manufacturer. The isolated RNA samples were dissolved in 8 µl of nuclease-free water and subjected to cDNA first-strand synthesis using SuperScript® III First-Strand Synthesis System for RT-PCR (Life Technologies, US) and manufacturer instructions. Finally, it yielded 20 µl of cDNA reaction per sample.

VH and VL Primers and PCR Amplification

The PCR reactions were performed in 50 µl using totally 35-40 cycles with Phusion Green Hot Start II High-Fidelity DNA Polymerase (Life Technologies, US) and pre-optimized conditions for each reaction. The primers for amplification of antibody VH and VL regions were designed in purpose to maximally cover the variety of VH and VL sequences. Primer pairs for amplification of the regions of chicken IgY were designed based on published data [Andris-Widhopf J, Rader C, Steinberger P, Fuller R, Barbas C F, 3rd: Methods for the generation of chicken monoclonal antibody fragments by phage display. *J Immunol Methods* 2000, 242(1-2):159-181], and used for amplification of VH and VL regions of chicken IgY. The mouse primer cocktails for amplification of VH and VLκ sequences were designed by published data [Schaefer J V, Honegger A, Plückthun A: Construction of scFv Fragments from Hybridoma or Spleen Cells by PCR Assembly. In: Antibody Engineering. Edited by Kontermann R, Diibel S, vol. 1, 2. edn. Heidelberg: Springer; 2010: 21-44.] and V- and J-region cDNA sequences made available in the international ImmunoGeneTics information System® (IMGT®) web resources [http://www.imgt.org/IMGTrepertoire]. For construction of scFv fragments, the rabbit VH and VL primer cocktails were designed by data in ref. [Rader C, Ritter G, Nathan S, Elia M, Gout I, Jungbluth A A, Cohen L S, Welt S, Old L J, Barbas C F, 3rd: The rabbit antibody repertoire as a novel source for the generation of therapeutic human antibodies. *J Biol Chem* 2000, 275(18):13668-13676.]; and the primers used for construction of libraries expressing intact rabbit IgG molecules were designed by rabbit sequences stored in IMGT® [http://www.imgt.org/IMGTrepertoire]. For cloning purposes, additional 20-23 nucleotides complementary to regions in the expression vector were added by primers to the ends of fragments that were joined with the other fragments. The VH reverse primers and VL forward primers used for scFv construction contained the regions in their 5' ends that formed coding sequence of flexible linker (GGGS)3 between VH and VL domains.

Construction of VH-VL Combinatory Libraries

Restriction/ligation independent Circular Polymerase Extension Cloning (CPEC) method [Quan J, Tian J: Circular polymerase extension cloning for high-throughput cloning of complex and combinatorial DNA libraries. Nat Protoc 2011, 6(2):242-251] was used for library construction by in-frame directed cloning of amplified VH and VL regions into the pQMCF mammalian expression plasmid (Icosagen Cell Factory, Estonia). The amplified variable domain sequences were mixed with the vector fragment(s) in the 20 µl reaction mixture. Five microliters were used for transformation of competent TOP10 F' or DH5α strain cells of *E. coli*. Approximately ⅒ of the transformation mixture was used for direct inoculation of 2 ml of selective carbenicillin containing liquid growth medium followed by extraction of plasmid DNA from the overnight culture (library pool). Another part of the transformation mixture was plated onto carbenicillin containing solid medium to obtain individual clones. The bacterial clones were amplified and plasmid DNA minipreparations were purified using Zyppy™-96 Plasmid Miniprep kit (Zymo Research, US) or FavorPrep™ 96-Well Plasmid Kit (Favorgen Biotech Corp., Taiwan) according to manufacturer's instructions.

Cells, Transfection and Sample Collection for Mammalian Screen

Chinese hamster ovary (CHO) cells derived cell line CHOEBNALT85 (Icosagen Cell Factory, Estonia) growing in serum-free chemically defined medium was used for mammalian screening. The cell line expresses EBV EBNA1 protein and polyomavirus large T protein and it is specifically designed for prolonged and high level production of proteins in association with pQMCF vectors. The cells were transfected using chemical transfection Reagent 007 (Icosagen Cell Factory, Estonia) according to the protocols provided by manufacturer [Karro K, Männik T, Männik A, Ustav M: DNA Transfer into Animal Cells Using Stearylated CPP Based Transfection Reagent. Methods Mol Biol 2015, 1324:435-445.]. One microgram of plasmid DNA was transfected in 6-well plate format for analysing library pools and approximately 0.2-0.5 µg DNA per sample was used in high-throughput 96-well plate transfection for screening of individual clones. Seventy-two hours after transfection the supernatants were collected for analysis. When necessary, scFv-Fc molecule concentration in the samples was determined using FastELISA for Human IgG quantification (RD Biotech, France).

ELISA

The ELISA plates (Nunc™ MaxiSorp™, Thermo Fisher Scientific, US) were coated at 4° C. overnight with antigen solution (5 µg/ml) or virus-like particle (VLP) suspension (20 µg/ml) in PBS, washed with washing solution (PBS containing 0.05% Tween 20), and incubated 1-2 h with blocking solution (PBS containing 2% BSA and 0.05% Tween 20) at room temperature. After washing the culture supernatants (diluted in blocking solution, if necessary) were incubated 1-2 h at room temperature. After washing 4 times, second incubation was performed with goat anti-human IgG (for scFv-Fc) or anti-rabbit IgG antibody conjugated with HRP (LabAs, Estonia). The signals were developed with TMB VII substrate (Biopanda Diagnostics, UK). The reactions were stopped by adding 0.5 M H2SO4 and absorbance values were measured at 450 nm.

Sequence Analysis

Protein sequences of identified antibody VH and VL sequences were analysed by exhaustive pairwise global alignments and progressive assembly of alignments using Neighbour-Joining phylogeny for similarity determination. This was done using Clone Manager Professional (Scientific & Educational Software) and BioEdit Sequence Alignment [Hall T A: BioEdit: a user-friendly biological sequence alignment editor and analysis program for Windows 95/98/NT. Nucl Acids Symp Ser 1999, 41:95-98.] software. Complementary determining regions (CDRs) in VH and VL amino acid sequences were determined using ref. [Andris-WidhopfJ, Rader C, Steinberger P, Fuller R, Barbas C F, 3rd: Methods for the generation of chicken monoclonal antibody fragments by phage display. J Immunol Methods 2000, 242(1-2):159-181.] and data in IMGT® web page [http://www.imgt.org/IMGTrepertoire].

The invention is now described by means of non-limiting examples. Reference is made to FIGS. 1-6.

Example 1. Capturing of Specific Antibody Expressing Cells

The capturing process is illustrated with examples using a spleen from chicken immunized with human DNase I protein, a mouse immunized with human artemin protein and a rabbit immunized with HPV18 E2 protein domain fused with GST (GST-HPV18 E2C).

The frozen sample was thawed and transferred into 10 ml of RPMI1640 cell culture medium in ambient temperature. The cells were collected by centrifugation (300×g, 5 min, room temperature), re-suspended in 10 ml of RPMI1640 supplemented with penicillin/streptomycin and 10% of heat inactivated foetal bovine serum (rabbit or mouse splenocytes) or chicken serum (chicken splenocytes). The cells were seeded into 100 mm cell culture dish and incubated ~1 h at 37° C. in 5-8% CO2 atmosphere. Plastic adherent cells were depleted from lymphocytes during the incubation and free-floating cells are carefully collected. Then the viable cells were counted using trypan blue exclusion. The cells were precipitated again by centrifugation and re-suspended in the capture medium. Only for chicken splenocyte preparations contaminated with high amounts of erythrocytes, additional Optiprep™ (60% iodixanol, Axis-Shield PoC AS, Norway) gradient purification was performed by sedimentation of lymphocytes to a density barrier before re-suspension in the capture medium.

MaxiSorp™ surface wells (Thermo Fisher Scientific, US) were coated with the antigen (20 µg/ml in PBS, 4° C., overnight) and blocked for 1-2 h with 2% BSA in PBS. One hundred microliters of cell suspension containing $2\times10^4$ living cells in capture medium were loaded into single well. As the capture medium we used is RPMI1640 supplemented with 0.5% BSA and 0.1% $NaN_3$. The plate was centrifuged (200×g, 5 min) for forcing the cells to antigen coated surface and let to bound to the antigen in ambient environment. We used pre-optimized ~45 min capturing time sufficient for cells bind to the antigen but not too long that can cause major degradation of cellular mRNA without de novo synthesis. Then the medium was discarded and loosely attached cells were removed by washing 4-5 times with PBS, each time pipetting gently up-down (3-4 times) in the edge of the well. Finally, the remained cells were lysed in wells and subjected to RNA isolation and cDNA preparation. We have found that starting from $2\text{-}6\times10^4$ mammalian splenocytes and $4\text{-}8\times10^4$ chicken splenocytes per single cDNA sample usually pretty optimal if animals are well immunized. In order to increase the number of recovered MAbs, setting up more capturing reactions is viable option instead of increasing the cell number per sample. Thus, material from 2 (mouse, rabbit) or 8 (chicken) wells were pooled together during RNA isolation.

Figure 2:
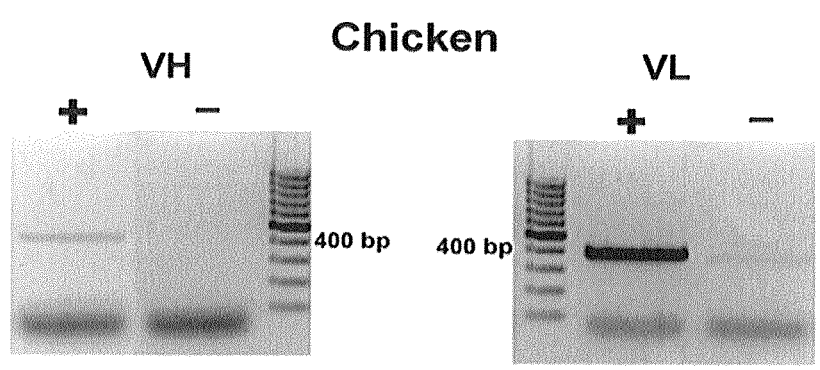
FIG. 2. Amplification of the VH and VL cDNAs from the spleen cells captured on antigen coated surface. The cDNAs were prepared from cells captured onto the antigen coated surface (+) and from control wells coated with BSA (−). A. Splenocytes from chicken immunized with human Dnase I protein B. Spleen homogenate from mouse isolated after immunization with human artemin protein. C. Spleen homogenate from rabbit immunized with GST-E2C fusion protein.
Figure 2:
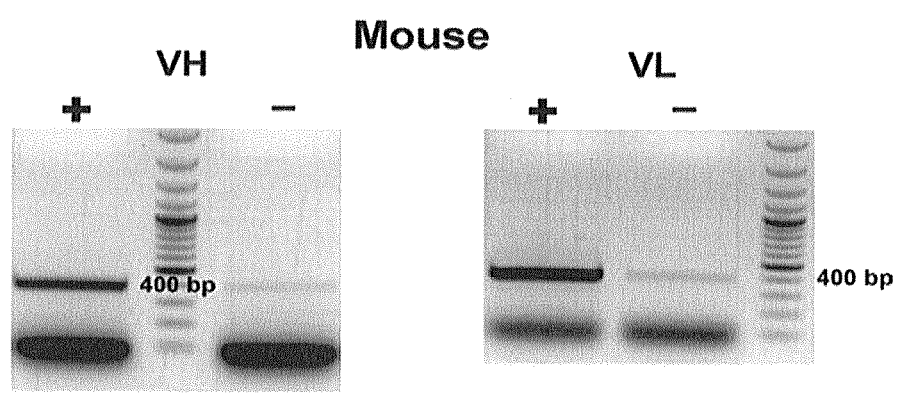
Figure 2:
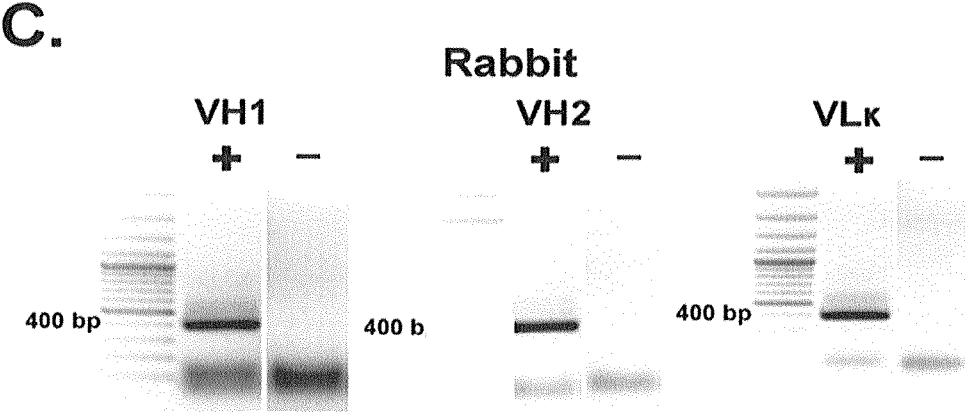
Figure 3:
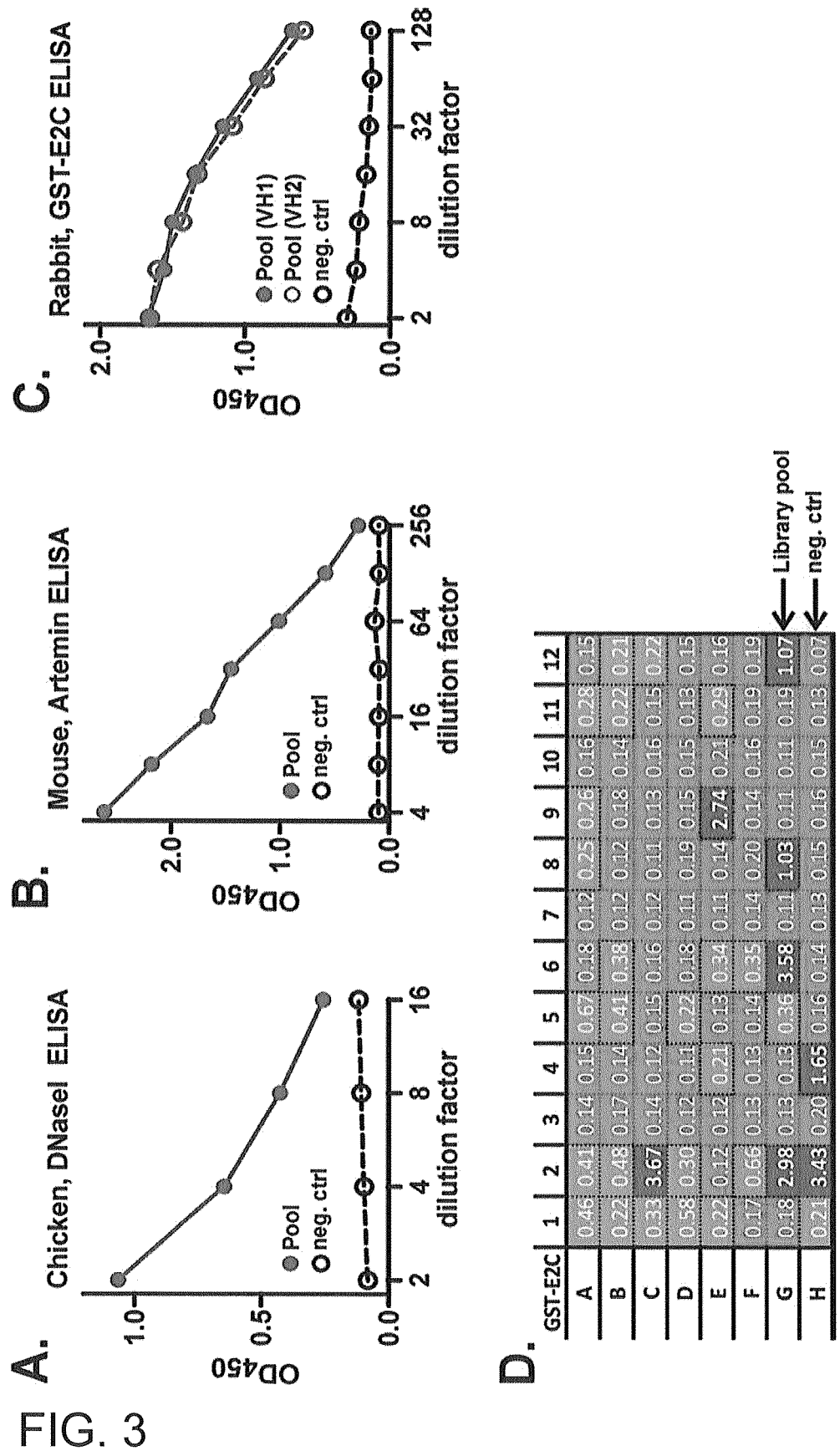
FIG. 3. Exemplary ELISA analyses of constructed scFv antibody libraries. A-C. The graphs represents ELISA results obtained using serial dilutions of 72 h time-point supernatants of CHOEBNALT85 cells transfected with 1 μg of HybriFree library pool DNAs constructed from VH and VL regions (shown in FIG. 2) amplified from captured cells: chicken immunized with human DNase I (A); mouse immunized with human artemin (B) and rabbit immunized with GST-E2C protein (C). Expression vector for non-relevant scFv-Fc vector was used as negative control in each transfection. D. Results of the single clone screening of the VH1 library pool showed in panel C. Wells G12 and H12 were transfected with library pool or negative control DNA, respectively.
Figure 4:
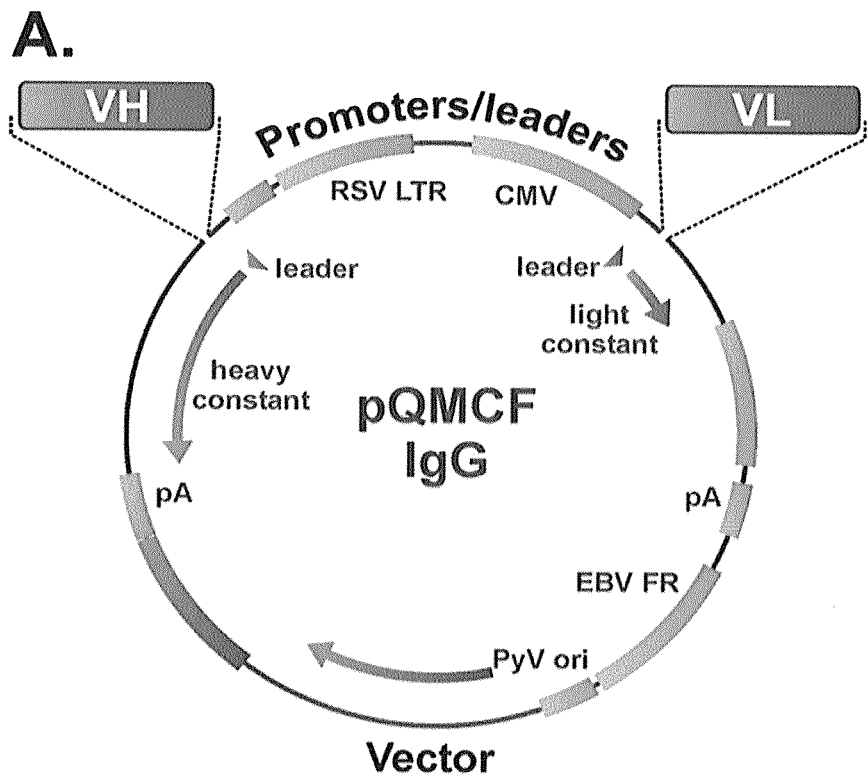
FIG. 4. Screening of natural IgG molecules. A. pQMCF IgG vector is constructed using single-step CPEC joining of 4 fragments: VH, VL, promoters/leaders and vector. The antibody heavy and light chain are expressed from the resulted vector as separate proteins which assemble into natural IgG molecules secreted from the mammalian cells. B. Western blot analysis of rabbit IgG secretion from CHOEBNALT85 cells transfected with pQMCF IgG library pool DNA constructed from VH and VL regions from rabbit immunized with mouse CD48 protein. The used pQMCF IgG vector contained rabbit IgG constant regions. Goat polyclonal antibody against rabbit IgG heavy chain was used for detection of free heavy chain in reduced sample conditions (DTT+) and assembled IgG molecul in non-reduced (DTT−) sample. C. Mouse CD48 ELISA results obtained using the serial dilutions of the same medium sample from library pool transfection as primary antibody.
Figure 4:
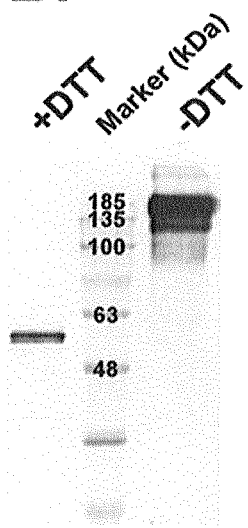
Figure 4:
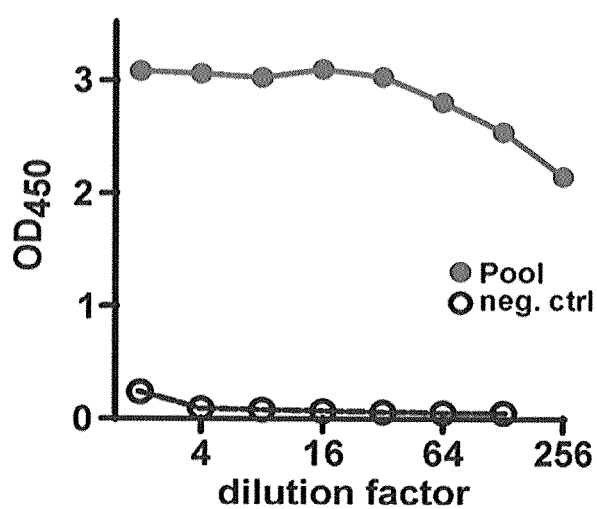
Figure 5:
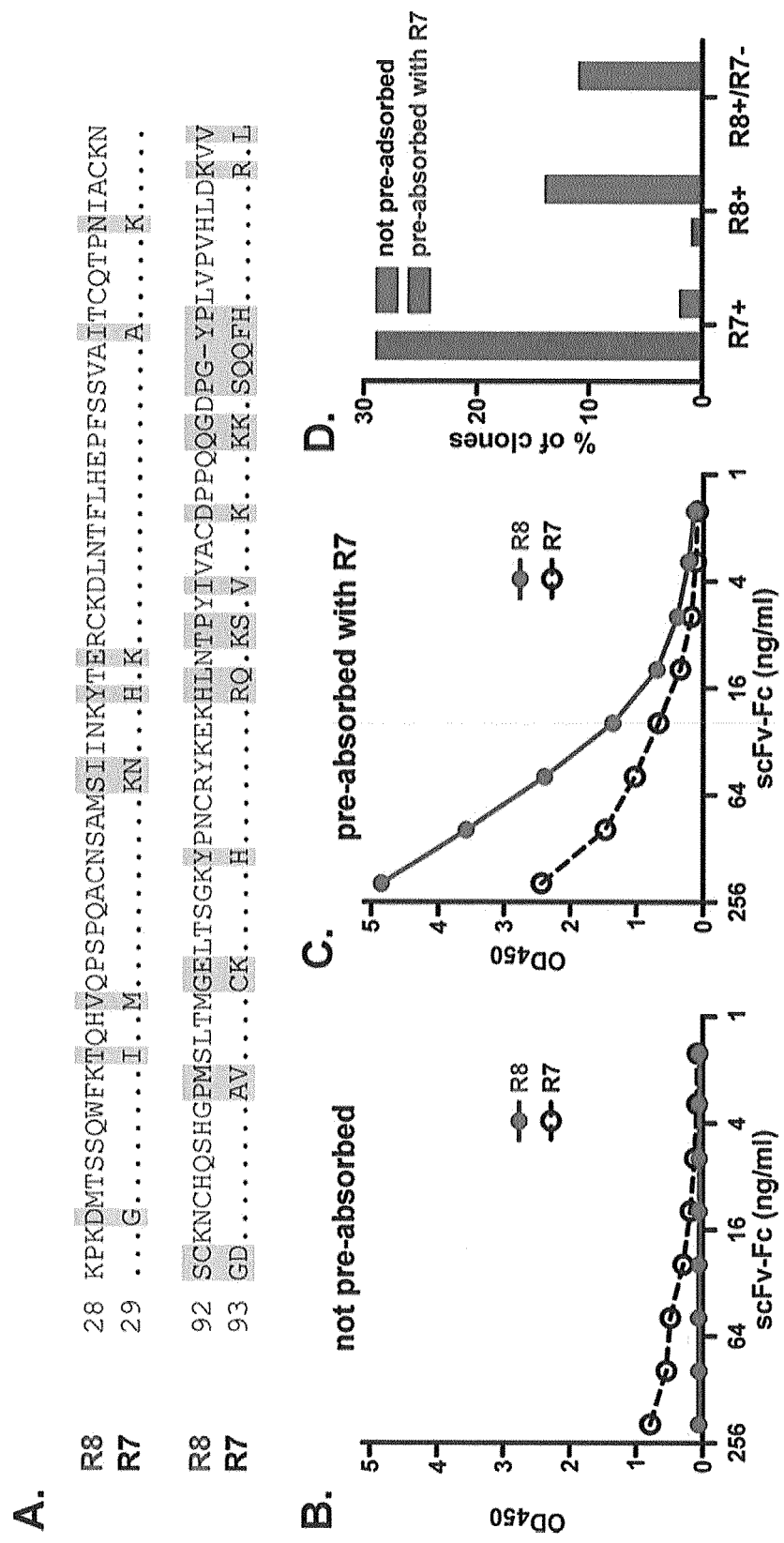
FIG. 5. Selective development of not cross-reactive antibodies using pre-adsorption step. A. Global alignment of mature protein sequences of human ribonuclease 8 (R8, UniProt ID: Q8TDE3) (SEQ ID NO:1) and ribonuclease 7 (R7, UniProt ID: Q9H1E1). B. ELISA assay result obtained using supernatants of CHOEBNALT85 cells transfected with 1 μg of library pool DNA derived from splenocytes captured without pre-adsorption step. C. Same ELISA assay but the library pool was from splenocytes captured with pre-adsorption step using R7 protein (100 μg/ml). D. Representation the percentage of R7-reactive (R7+), R8-reactive and only R8-reactive (R8+/R7−) scFv-Fc clones retrieved from pre-adsorbed and control library, respectively.
Figure 6:
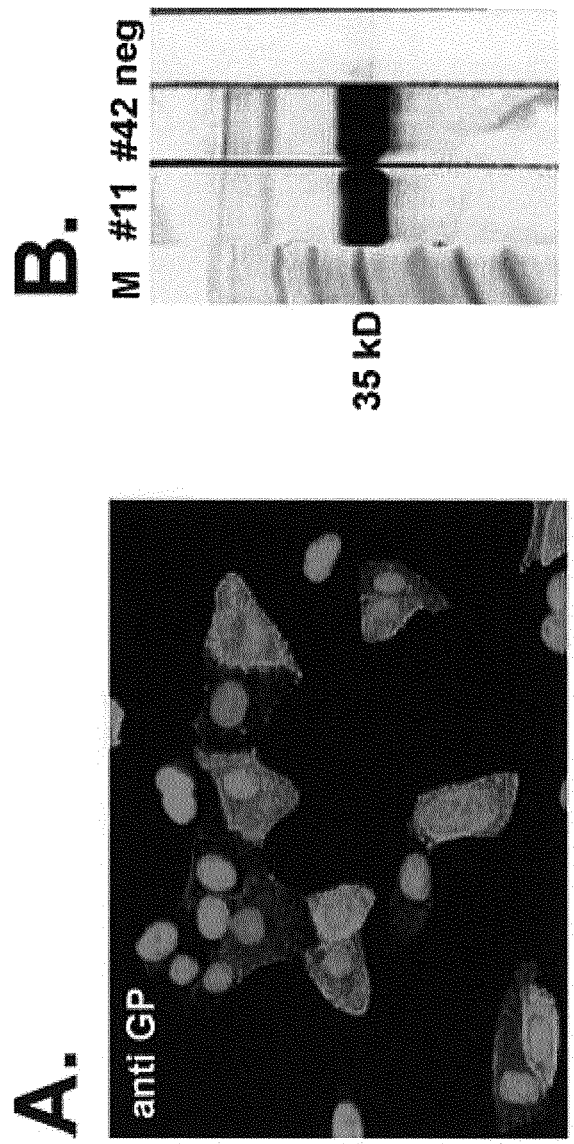
FIG. 6. A. MAb derived from rabbit immunized with Ebola virus VLPs works as sensitive and selective reagent for visualization of Ebola virus glycoprotein (GP) expression (green) in human cells by immunofluorescence. Nuclei are counterstained with DAPI (blue). B. Anti-human Dnase I IgY antibodies were re-constructed from developed MAb sequences from chicken. These were produced in CHO cells and can be used for detection of ~35 kD hDNase I band in Western blot assay (expression vector producing non-relevant IgY is used as negative control here).

The success of antigen-specific cell capturing was first suggested by agarose gel electrophoresis of ~400 bp VH and VL amplification products showed in FIG. 2A-C. In lanes marked by (+) the cells were captured on the relevant target antigen. As control reactions, the identical capturing procedures were also performed using BSA as non-relevant protein (lanes marked with (−) in FIG. 2). Comparing the signal intensities of PCR products between (+) and (−) lanes in FIG. 2, it is obvious, that in case of all source animals the VH and VL products were amplified only or much more efficiently when the cells were from (+) wells.

Example 2. scFv-Fc Library Construction and Screening of MAbs

Next, VH-VL combinatorial libraries were constructed from amplified VH and VL regions showed in FIG. 2 using CPEC technique. For rabbit splenocytes, two PCR reactions (VH1 and VH2) were used for better coverage of VH cDNAs (FIG. 2C). Thus, two separate cloning reactions were performed by combining VH1 product or VH2 product with VLκ product. During the CPEC reaction of 3 fragments (vector, VH, VL) pQMCF scFv-Fc vectors were formed via random pairing of VH and VL fragments and in-frame joining of scFv cDNA 5' and 3' end with mouse immunoglobulin heavy chain secretion leader peptide cDNA and human IgG1 Fc region cDNA, respectively (step 3 in FIG. 1). The CPEC reaction is initiated by annealing and extending of complementary DNA strands in the ends of joined DNA fragments. Thus we added the sequence from the 3' end of leader peptide cDNA to the 5' end of the VH fragment (during the PCR reaction from cDNA) and sequence from 5' end of the Fc region to the 3' end of the VL fragment to initiate the joining of the 3 fragments without additional nucleotides between the vector and the insertion. Similarly, the flexible linker $(GGGGS)_3$ is created between the VH and VL. In the examples described here, the expression of the scFv-Fc was controlled by Rous sarcoma virus long terminal repeat as promoter. Library pool samples (mixture of all library members) and single clone DNA minipreparations (using a convenient high-throughput 96-well method) were prepared from E. coli cells directly transformed with CPEC reaction. PCR analysis of bacterial colonies showed high efficiency of the cloning and routinely >90% of CPEC clones contain directed VH-VL insertion in the vector (data not shown).

The efficiency of the antigen specific MAb reconstruction from the VH and VL combinations was initially analysed by transfection of library pools. The DNAs were transfected into the CHOEBNALT85 cells and 72 h later the culture supernatants were assessed in ELISA for the secretion of antigen recognizing scFv-Fc molecules. As seen in FIG. 3A-C, the positive signals qualitatively different from the controls were observed in all samples suggesting the presence of proper MAbs in the libraries. As next step, the individual MAbs with specific affinity were identified by screening of plasmid DNA minipreparations derived from single clones. One or two 96 well plates (including appropriate positive and negative controls) were analysed per each library. The positive signals we determined arbitrarily as at least 2-3 times over the negative control (empty expression vector or expressing a non-relevant scFv-Fc). However, measured at time-point 72 h after transfection, the positive signals typically qualitatively discriminated from the negative samples by giving 10 or more times higher readouts (FIG. 3D). Between different antigens and animals the efficiency of the screening (percentage of positive hits) in our experiments have varied between 7% and 60%.

Example 3. Screening of Natural IgG Molecules

For cloning of the libraries expressing natural IgG molecules instead of scFv-Fc, the CPEC strategy was modified to direct in-frame joining of the 4 fragments (VH, VL, promoters/leaders, and vector). Here the VH and VL are both joined with secretion leader peptide cDNA at their 5' end and constant domain cDNA at 3' end without additional nucleotides between the vector and the insertion. Final product from CPEC reaction is the pQMCF IgG vector with separate expression cassettes for IgG heavy and light chain, respectively (FIG. 4A). To ensure the efficient CPEC assembly, the complementary regions in the end of the fragments were carefully optimized using synonymous replacements in leader peptide and constant region cDNAs. The modification of the method is illustrated here by the development of rabbit MAbs against mouse CD48 protein. VH and VL fragments were created from the spleen cells captured on mouse CD48 coated wells. The cloning reaction was performed using pQMCF IgG vector containing rabbit IgG heavy and light (kappa) chain constant region codon optimized cDNAs. The formed IgG heavy and light chain was expressed under control of RSV LTR and CMV promoter, respectively. Initial restriction analysis of library pool DNA and colony PCR from 38 individual bacterial colonies indicated 100% efficiency of the pQMCF IgG vector assembly from the 4 fragments. Western blot analysis of the culture medium sample from library pool DNA transfected CHO85EBNALT cells confirmed the predominance of intact rabbit IgG molecules assembled from the separately expressed heavy and light chains (FIG. 4B). Analysis of the same library pool transfection medium sample in mouse CD48 ELISA demonstrated the presence of antigen specific antibodies (FIG. 4C). Finally, analysis of 95 bacterial clones resulted >50% of wells as strongly positive and gave OD values >3.0 vs. OD=0.1 in negative control well.

Example 4. Selective Capturing Using the Pre-Adsorption of Source Cells

To illustrate how the technology of this invention can be used for recovery of very specific MAbs the development of MAbs against human ribonuclease 8 (R8) protein from spleen cells of the immunized rabbit is described here. The goal was to obtain anti-R8 MAbs that have minimal cross-reactivity with highly homologous human ribonuclease 7 (R7) (FIG. 5A) and thus pre-adsorption step with R7 was included before the cell capturing. Precisely, the R8 protein immunized rabbit spleen cells were captured in two ways: just using R8 coated surface and capture medium as described in the section "Capturing of antigen specific B-cells" above; or by supplementing the medium with R7 protein (100 μg/ml) and including short (15 min) pre-adsorption step in suspension before the cells were centrifuged to R8 coated bottom of the wells. As illustrated in FIG. 5B, the library pool from not pre-adsorbed cells gave relatively low readouts at all. Most surprisingly the responses were even higher for R7 protein and the readouts of R8 protein binding were just faintly over the background. This may indicate that dominant antigenic epitopes in the R8 protein exposed in vivo were not equally available in plastic bound antigen in vitro. In contrast, potent anti-R8 response was detected in library pool obtained using pre-adsorption with R7 protein. There was also some response to the R7 but the titre was significantly higher for R8 (FIG. 5C). Ninety-two individual clones were screened from either library for binding to R8 and R7 protein, respectively. The results showed in FIG. 5D were in accordance with data of library pool analyses. The R7-reactive MAbs with weak readouts dominated in library prepared without pre-adsorption and R8-reactive hits were prevalent when the pre-adsorption was used. Only from pre-adsorbed pool we found desired MAbs reacting with the R8 but having no or low cross-reactivity with R7 protein (R8+/R7− in FIG. 5D).

We believe that this kind of pre-adsorption should be also useful for screening of antibodies from organisms immunized with complex antigens. For example, using the viral surface proteins pseudotyped VLPs instead of just purified surface proteins for immunization generally gives better chances to arise the virus neutralizing antibodies [30]. Using the same VLPs for capturing of antigen expressing cells as well as for screening, give opportunity to isolate and clone such antibodies. However, using VLPs for immunization usually results in mixed response including many MAbs specific to off-targets, e.g. directed to structural components of the VLPs. Thus, it may be useful to inhibit the recovery of the off-target antibodies by pre-adsorption of the antibody expressing source cells with non-pseudotyped VLPs.

The budding of VLPs is induced by intracellular expression of viral structural protein, like retroviral (e.g. HIV or murine leukaemia virus) gag protein or Ebola virus VP40 protein, as non-limiting examples. If the same cells also express a protein consisting in extracellular domain and membrane associated domain, this protein can be incorporated (pseudotyped) into the VLPs such that the extracellular domain is exposed on the surface of the VLPs. For example, this kind of protein consisting in extracellular domain and membrane associated domain can be a viral surface protein or cellular protein or artificial chimeric protein constructed by recombinant fusion of membrane associated domain and extracellular domain. The pseudotyped VLP can be used as effective immunogen for induction of antibody response against the extracellular domain exposed on the surface. As the pseudotyped protein on the VLPs resembles the exposing the protein on the viral particles, using the strategy with viral surface proteins (or extracellular domains of these) there is good chance to induce the antibodies that recognize the protein when it is exposed in its natural milieu in the viral particle. Thus, using such VLPs for immunization as well as for MAb isolation by the invention increase the chances to isolate anti-viral neutralizing antibodies. However, using VLPs for immunization usually results mixed response including many off-target specific MAbs directed to structural components of the VLPs instead of the pseudotyped surface protein. To avoid screening of these MAbs but enrich to MAbs against the target protein, preadsorbtion step is used as described in Example 4. Here the "empty" or non-pseudotyped VLPs produced by expression of structural protein only are used for pre-adsorption. Thereafter the source cells are captured using the same VLPs but pseudotyped with target immunogen.

Example 5. Validation and Sequence Analysis of the MAbs Obtained by the Method

We have successfully practiced the HybriFree method using immunized mammals and birds as well as different viral and cellular antigens. The variety of MAbs we have developed by the method include those recognizing linear epitopes and are useful for detection in assays like immunofluorescence (FIG. 6A) and immunoblotting (FIG. 6B). The target antigens include viral protein, like Ebola virus glycoprotein and human papillomavirus E2 protein as well as human cellular proteins, like (artemin, CD48, DNaseI, ribonuclease 8, Nerve Growth Factor). The antibodies include also those binding to conformational epitopes and have potential interest in development of products with biological activity. Using the sequence information obtained by method we have produced scFV-Fc antibodies and natural IgG and IgY antibodies in larger scales production in CHO85EBNALT cells and purified.

Example 6: Monoclonal Antibodies Specific to Ebola Virus Full-Length Glycoprotein The rabbit was immunized with VLPs produced by expression of Ebola virus VP40 protein in human 293 cells. Due to co-expression of Ebola virus full-length glycoprotein (GP), the VLPs were pseudotyped with proteolytically correctly processed GP. The VLPs were precipitated from the serum-free culture supernatant, re-suspended in PBS and used directly from immunization. After 4 round of immunizations and boost with purified GP, the significant anti-GP response was detected in blood serum. The spleen was collected and prepared as described in Methods above. The cell capturing was performed on the GP pseudotyped VLPs coated to the bottom of MaxiSorp wells as described in example 1, but including 10 min pre-incubation step preceding the capturing. During this pre-incubation step the source spleen cells were incubated with gently mixing in capture medium containing the Ebola virus VLPs (50 μg/ml) produced by expression of only the VP40 protein, but not the GP in the same 293-cells. It was expected that during this pre-adsorption step the binding sites of surface immunoglobulins that are directed to other components of VLP than GP are saturated and thus cannot be reactive in the next capturing step. After capturing the sample was processed as described in Examples 2 and 3 and this yielded MAbs that were specific to GP and recognize the GP present on the VLPs.

What is claimed is:

1. An in vitro method to develop monoclonal antibodies, said method comprising the steps of:
   a) capturing source cells expressing antigen specific antibodies from crude spleen homogenate, bone marrow, or peripheral blood cells from immunized animals on a solid matrix covered with the antigen in a capturing media comprising BSA and $NaN_3$;
   b) amplifying variable heavy chain (VH) and variable light chain (VL) cDNA from the captured cells;
   c) constructing a VH-VL combinatory library in a mammalian expression vector;
   d) identifying proper VH-VL combinations by using mammalian screen; e) Construction of authentic monoclonal antibody from the VH and VL amplified sequences; and
   f) identifying proper target-specific antibody expressed from the mammalian cells using the mammalian screen.

2. The method of claim 1, wherein the mammalian expression vector is a QMCF vector.

3. The method of claim 1, wherein in the step d) the mammalian screen is conducted in CHO-derived cell line on a multi-well plate.

4. The method of claim 3, wherein the cell line is CHOEBNALT85-cell line.

5. The method of claim 1, wherein in step a) the number of cells in the well is $2 \times 10^4$ to $8 \times 10^4$.

6. The method of claim 1, wherein step a) is preceded by a pre-adsorption step of the source cells in a medium containing one or more off-target proteins.

7. The method of claim 6, wherein the pre-adsorption step is about 15 minutes after which the cells are centrifuged and transferred into to step a) of claim 1.

8. The method of claim 1, wherein the animals are immunized with a pseudotyped VLP and the monoclonal antibodies developed are virus neutralizing antibodies.

9. The method of claim 8, wherein the virus neutralizing antibodies are against HPV, Ebola, Chikungunya, or HIV.

10. A method to produce monoclonal antibodies, wherein the antibodies are developed according to claim 1, and the mammalian cells identified in step d) are further cultured in large scale for antibody production.

11. The method of claim 10, wherein the antibodies are free from off-target affinity.

* * * * *

UNITED STATES PATENT AND TRADEMARK OFFICE
CERTIFICATE OF CORRECTION

Page 1 of 1

PATENT NO. : 10,995,134 B2
APPLICATION NO. : 15/764990
DATED : May 4, 2021
INVENTOR(S) : Gaily Kivi et al.

It is certified that error appears in the above-identified patent and that said Letters Patent is hereby corrected as shown below:

On the Title Page

Item (73), should read:
(73) Assignee: Icosagen Cell Factory OÜ, Ülenurme (EE)

Signed and Sealed this
Twenty-sixth Day of April, 2022

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 127
<212> TYPE: PRT
<213> ORGANISM: Homo sapiens
<220> FEATURE:
<221> NAME/KEY: PEPTIDE
<222> LOCATION: (1)..(127)
<223> OTHER INFORMATION: Human ribonuclease 8 amino acid sequence
      starting at position 29

<400> SEQUENCE: 1

Lys Pro Lys Asp Met Thr Ser Ser Gln Trp Phe Lys Thr Gln His Val
1               5                   10                  15

Gln Pro Ser Pro Gln Ala Cys Asn Ser Ala Met Ser Ile Ile Asn Lys
                20                  25                  30

Tyr Thr Glu Arg Cys Lys Asp Leu Asn Thr Phe Leu His Glu Pro Phe
            35                  40                  45

Ser Ser Val Ala Ile Thr Cys Gln Thr Pro Asn Ile Ala Cys Lys Asn
        50                  55                  60

Ser Cys Lys Asn Cys His Gln Ser His Gly Pro Met Ser Leu Thr Met
65                  70                  75                  80

Gly Glu Leu Thr Ser Gly Lys Tyr Pro Asn Cys Arg Tyr Lys Glu Lys
                85                  90                  95

His Leu Asn Thr Pro Tyr Ile Val Ala Cys Asp Pro Pro Gln Gln Gly
                100                 105                 110
```

```
Asp Pro Gly Tyr Pro Leu Val Pro Val His Leu Asp Lys Val Val
        115                 120                 125
```